United States Patent
Lee et al.

(10) Patent No.: US 9,770,177 B2
(45) Date of Patent: Sep. 26, 2017

(54) RING-TYPE CUFF FOR BLOOD PRESSURE MANOMETER

(71) Applicants: Byung Hoon Lee, Seoul (KR); Jae Cheon Lee, Cheju-do (KR)

(72) Inventors: Byung Hoon Lee, Seoul (KR); Jae Cheon Lee, Cheju-do (KR)

(*) Notice: Subject to any disclaimer, the term of this patent is extended or adjusted under 35 U.S.C. 154(b) by 491 days.

(21) Appl. No.: 14/378,685

(22) PCT Filed: Feb. 15, 2013

(86) PCT No.: PCT/KR2013/001196
§ 371 (c)(1),
(2) Date: Aug. 14, 2014

(87) PCT Pub. No.: WO2013/122417
PCT Pub. Date: Aug. 22, 2013

(65) Prior Publication Data
US 2016/0022158 A1    Jan. 28, 2016

(30) Foreign Application Priority Data
Feb. 16, 2012 (KR) .......................... 10-2012-0015873

(51) Int. Cl.
*A61B 5/021* (2006.01)
*A61B 5/00* (2006.01)

(52) U.S. Cl.
CPC ........ *A61B 5/02141* (2013.01); *A61B 5/6824* (2013.01); *A61B 5/6829* (2013.01);
(Continued)

(58) Field of Classification Search
None
See application file for complete search history.

(56) References Cited

U.S. PATENT DOCUMENTS 5,351,694 A * 10/1994 Davis ................. A61B 5/02241
600/485
6,151,968 A * 11/2000 Chou ..................... A61B 5/681
73/748
(Continued)

FOREIGN PATENT DOCUMENTS

JP          4544917 B2      7/2010
KR    10/2006-0046487 A    5/2006
(Continued)

OTHER PUBLICATIONS

Korean Patent Laid-open Gazette 10-2005-0107506, "A Cuff System for Measuring Blood Pressure and a Sphygmomanometer Including the Same", Nov. 11, 2005.
(Continued)

*Primary Examiner* — Jacqueline Cheng
*Assistant Examiner* — Jairo Portillo
(74) *Attorney, Agent, or Firm* — Baker & Hostetler LLP

(57) ABSTRACT

The present invention relates to a ring-type cuff for blood pressure manometer, wherein the cuff (C) comprises: a circular rubber ring (1) wearable on a wrist or an ankle; a resilient coil spring (2) built-in inside the tubular rubber ring (1) in the range of length of the rubber ring to obtain a predetermined flexibility, to suppress excessive stretching, to strengthen durability, and to maintain resilience; and a measurement portion (3) comprising a pressure sensor (S) for measuring blood pressure, a transmission circuit (IC) for transmitting measurement data to the outside, a power source (v), a power switch (sw), and a pilot lamp (LED). The ring-type cuff (C) is worn on the wrist or the ankle at ordinary times; when measuring blood pressure, the ring-type cuff (C) is placed on a measurement site to be fixed by a self-elastic supporting force, blood pressure is measured by the pressure sensor (S) of the measurement portion (3) and the pilot lamp (LED) is simultaneously lighted, the
(Continued)

measured data is wired and wirelessly transferred to an external sphygmomanometer by the transmission circuit (IC) to be analyzed, and the analyzed result is displayed on a display portion through a letter or a figure; and the pilot lamp is also turned off if the ring-type cuff (C) descends to the wrist after measurement.

17 Claims, 3 Drawing Sheets

(52) U.S. Cl.
CPC .......... *A61B 5/6831* (2013.01); *A61B 5/0002* (2013.01); *A61B 5/0004* (2013.01); *A61B 5/7475* (2013.01)

(56) References Cited

U.S. PATENT DOCUMENTS

| | | | |
|---|---|---|---|
| 7,250,030 B2 | 7/2007 | Sano et al. | |
| 2002/0183646 A1* | 12/2002 | Stivoric | A61B 5/0008 600/549 |
| 2004/0116837 A1* | 6/2004 | Yamaguchi | A61B 5/02438 600/595 |
| 2005/0283084 A1* | 12/2005 | Kato | A61B 5/02233 600/499 |
| 2007/0060826 A1* | 3/2007 | Krauter | A61B 5/0235 600/498 |
| 2008/0312544 A1* | 12/2008 | Mochizuki | A61B 5/022 600/492 |
| 2010/0210956 A1 | 8/2010 | Im | |
| 2011/0257928 A1* | 10/2011 | Cunningham | A61B 5/1116 702/150 |
| 2012/0197139 A1 | 8/2012 | Lee | |

FOREIGN PATENT DOCUMENTS

| | | |
|---|---|---|
| KR | 10/2006-0114866 A | 11/2006 |
| KR | 10/0847898 B1 | 7/2008 |

OTHER PUBLICATIONS

Korean Utility Model Gazette 1990-0007450 "A Cuff System for Measuring Blood Pressure", Aug. 18, 1990.
Korean Patent Gazette 10-0666807, "A Cuff for Blood Pressure Measuring System and a Blood Measuring System Having the Cuff", Jan. 9, 2007.
Korean Patent Gazette 10-1016220, "A Device for Blood Pressure Measurement", Feb. 28, 2011.
Korean Patent Gazette 10-1081659, "An Auto-Diagnostic Blood Manometer", Nov. 9, 2011.

\* cited by examiner

RING-TYPE CUFF FOR BLOOD PRESSURE MANOMETER

CROSS-REFERENCE TO RELATED APPLICATIONS

This application is the National Stage of International Application No. PCT/KR2013/001196 filed Feb. 15, 2013 which claims the benefit of Korean Application No. 10-2012-0015873 filed Feb. 16, 2012, the disclosures of which are incorporated herein by reference in their entireties.

TECHNICAL FIELD

The present invention generally relates to a sphygmomanometer, more specifically to a ring-type cuff for blood pressure manometer.

BACKGROUND OF THE INVENTION

In general, a sphygmomanometer or a cuff having a pressure sensor for blood pressure measurement is composed of a wearable tube with a certain length. The tube forms an internal space to be filled with air and equipped with a small motor pump at one side of the tube. In order to determine blood pressure, a cuff is normally placed around an upper arm to pressure the measurement site of the arm and about 180 mmHg air is injected into the cuff. As the pressure in the cuff falls, a pressure sensor measures blood pressures at the periods of cardiac contraction and cardiac dilation.

The followings are examples of prior arts:

According to Korean Utility Model Gazette 1990-0007450 (published dated Aug. 18, 1990), "a cuff system for measuring blood pressure" is directed to a sphygmomanometer for a finger by pressuring an artery of the finger. The cuff system comprises a cuff for pressuring a human body (i.e. finger), a photoelectric device placed in the pressured air of the cuff to detect a pulse signal, a signal transfer part that transfers the pulse signal to an electronic circuit part of the cuff by connecting one side of the signal transfer part to the photoelectric device and connecting the other side of the signal transfer part to the electronic circuit part, wherein the signal transfer part further comprises a flexible substrate having a conductor pattern on its substrate. As the cuff is pressured, the flexible substrate contracts and expands in the vertical direction. Thus, the signal transfer part is not affected by a tensile load when connecting the pulse signal to the electronic circuit part.

According to Korean Patent Laid-open Gazette 10-2005-0107506 (published dated Nov. 11, 2005), "a cuff for measuring blood pressure and a sphygmomanometer including the same" is directed to providing blood pressure measurement by simply setting up the winding condition of the cuff according to the thickness of a measuring site. Said technology comprises a plurality of marks to display the winding condition of the cuff according to the perimeter length of the measuring site, and a window frame member that selectively indicates one mark from the plurality of marks. The cuff part where the plurality of marks is formed slides between the warped surface of the cuff part where the window frame member is adhered and the window frame member. In that way, one mark is selectively displayed through the window frame member. Thus, the winding condition (the diameter of the cylindrical form of the cuff) of the cuff according to the perimeter length (the thickness) of the measuring site is simply controlled by setting up the window frame member.

According to Korean Patent Gazette 10-0666807 (announced dated Jan. 9, 2007), "a cuff for blood pressure measuring system and a blood pressure measuring system having the cuff" comprises a fluid part where the fluid expands and contracts in the thickness direction as the fluid part moves in and out. The fluid part includes a first bag positioned in the outer side of the thickness direction having a first expansion and contraction portions internally when the cuff is installed on an organism, and a second bag positioned in the inner side of the thickness direction having a second expansion and contraction portions internally when the cuff is installed on the organism. The second bag superposes a single-layered sheet shape member of the first bag. The bag is formed by welding the periphery to the surface of the organism. The sheet shape member and its junction are internally located on both end portions of the first expansion and contraction portions.

According to Korean Patent Gazette 10-10106220 (announced dated Feb. 28, 2011), "a device for blood pressure measurement" comprises a measurement unit that periodically measures blood pressure and wirelessly transmits the measured blood pressure, and a storage unit separated from the measurement unit to record the measured blood pressure that is wirelessly transmitted by the measurement unit. The measurement unit further comprises an attach unit having a shape of a wrist attachable band, a tape, or a wristwatch and multiple blood pressure measurement units to be combined in the attach unit. The multiple blood pressure measurement units are equipped with a pressure sensor comprising a first electrode layer, a first insulation part, a second electrode layer, a second insulation part, and a conductor. The storage unit includes a transmission part that converts a measured capacitance change into a resonant frequency, a power supply, a frequency detection part, a translation part, and a memory storage unit.

According to Korean Patent Gazette 10-1081659 (announced dated Nov. 9, 2011), "an auto-diagnostic blood manometer" comprises a pressure control sensor to control air pressure of a cuff to measure blood pressure, a pulse measurement sensor, a central control unit that processes measured data that is transmitted by the pressure control sensor and the pulse measurement sensor. The central control unit is capable of displaying high, normal, or low blood pressures based on the measurement data transmitted by the pressure control sensor. The central control unit is also capable of displaying pulse measurements of vein, arrhythmia, pyknocardia, or bradyrhythmia based on the measured data transmitted by the pulse measurement sensor. The cuff can display the results of measurement data via text and simultaneously store and transmit the results of measurement data.

As explained above, most of the cuffs for blood pressure measurement system are composed of a tube that is filled with an air, an air motor pump to control air pressure, and additional means. Thus, in order to measure blood pressure by a blood pressure sensor, an operator has to perform an action of winding the cuff around measuring site, injecting air into the tube to pressure the measuring site, and reducing the air pressure by the pressure of the expanding cuff after pressuring the measuring site. These procedures are likely complicated and cumbersome for the operators.

Although some cuffs are formed after a band or tape, those cuffs require an operator to manually wrap the band or tape around the measuring site to measure blood pressure. Moreover, there have been difficulties in carrying those cuffs.

Especially for hypertensive patients who are required to measure their blood pressures frequently or in the long-term, operating such procedures is inconvenient and cumbersome.

SUMMARY OF THE INVENTION

The present invention is directed to providing a flexible ring-type cuff for blood pressure manometer, which can replace the tube-type cuff in the 'auto-diagnostic blood manometer' of the aforesaid Korean Patent Gazette No. 10-1081659.

Furthermore, the present invention is directed to providing a flexible ring-type cuff for blood pressure manometer that can be used with a wireless or wired manometer.

The ring-type cuff of the present invention comprises a flexible tubular ring made of rubber. The rubber ring has a resilient coil spring built-in inside the rubber ring to strengthen functions of the rubber ring. The flexible ring-type cuff is 60 mm to 80 mm in diameter and 5 cm to 8 cm in the thickness. The coil spring in the cuff has a function of maintaining its self-elastic supporting force by maintaining the original shape of the coil spring and preventing deterioration due to the flexibility of the coil spring.

A measurement portion for blood pressure is located at a certain portion of the ring-type cuff and comprises a transmission circuit for transmitting measured data, a power source, and a power switch that is on by a tension force of the coil spring. The ring-type cuff can be applied to a general sphygmomanometer. In order to apply in the general sphygmomanometer, the measurement portion includes a jackhole that can be connected to the general sphygmomanometer through a plug. The measurement portion also transfers the measured data measured by the pressure sensor to an external sphygmomanometer through the plug that is connected to the jackhole. Moreover, the transmission circuit of the measurement portion can wirelessly transfer the measured data to a wireless sphygmomanometer.

The measured data transmitted by the measurement portion of the present invention are received at and analyzed by the central control unit of the 'auto-diagnostic blood manometer' of the aforesaid patent. The name of disease as the result of diagnosis is displayed on a display portion through a letter or a figure. Because the result of diagnosis can be applied to other blood pressure manometers, it is the same that other blood pressure manometers display the result of diagnosis based on the measured data transmitted from the measurement portion of the ring-type cuff.

The present invention includes a cuff, a pressure sensor, etc. However, when the ring-type cuff of the present invention is used, the central control unit analyzes the measurement data and the display unit shows the name of disease according to the result of diagnosis. Thus, the 'auto-diagnostic blood manometer' of the aforesaid patent can be used independently and can be applied herein with the ring-type cuff of the present invention.

The ring-type cuff of the present invention is appropriate for the hypertensive patients who are required to measure their blood pressures frequently or in the long-term. Since the present invention is formed after a bracelet of ornament, one can always wear the ring-type cuff of the present invention on one's wrist or ankle. Although one wears the ring-type cuff around the wrist or ankle, it is not an obstacle for one's daily activities because the ring-type cuff is light. Furthermore, because the diameter of the ring-type cuff is larger than that of the wrist or ankle, the tension force of the ring-type cuff does not work while wearing the ring-type cuff Thus, the present invention does not include additional procedures to measure blood pressure and rarely consumes electricity.

When measuring blood pressure, one may move the ring-type cuff toward his or her forearm or calf. At this time, the ring-type cuff increases its size in response to the changes of the size on measuring sites of the human organism. And then, it is fixed at the measuring site by a self-elastic supporting force. At this moment, the pressure working on the measuring site of the human organism is light, only 30 g to 100 g to the whole length of the ring-type cuff. The power switch of the measurement portion is connected on when the size of the ring-type cuff is increased. The pilot ramp is turned on and the pressure sensor is activated so that one can measure blood pressure day and night. In this case, unlike prior rubber cuffs, the ring-type cuff does not intensely pressure the measuring site. Thus, it does not inflict pain of pressure by the cuff on the wearers while they are measuring their blood pressures. The pressure sensor measures blood pressures at the periods of cardiac contraction and cardiac dilation.

The transmission circuit sends the measured data measured by the pressure sensor to the outside. The central control unit of the 'auto-diagnostic blood manometer' of the aforesaid patent inputs and analyzes the measured data. According to the result of analysis, the display unit presents the name of disease on a display portion.

In addition, the measured data can be transmitted directly to other blood pressure manometers by connecting the other blood pressure manometers to the jackhole of the measurement portion.

After completing the blood pressure measurement, if the ring-type cuff is moved back to the wrist or ankle where the ring-type cuff was originally positioned, the ring-type cuff returns to the original state as it contracts its tension force. The power switch that was connected on as the size of the ring-type cuff was increased is now disconnected, thereby suppressing power consumption of the ring-type cuff Thus, one who wears the ring-type cuff is able to measure his or her blood pressure repeatedly or frequently with a simple operation.

By the present invention in which the ring-type cuff for blood pressure manometer comprises a flexible tubular ring made of rubber, one can simply measure his or her blood pressure by wearing it around his or her wrist or ankle and frequently turning on its pilot ramp.

Furthermore, the ring-type cuff can be used durably because the present invention has a resilient coil spring built-in inside the ring-type cuff. This means that the resilient coil spring maintains the original shape of the coil spring, strengthens its durability, and prevents deterioration due to the flexibility of the coil spring Because the structure of ring-type cuff is extremely simple, the present invention is mobile, durable, and ornamental when it is worn around a wrist or an ankle. Thus, anybody can use this ring-type cuff for blood pressure manometer.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
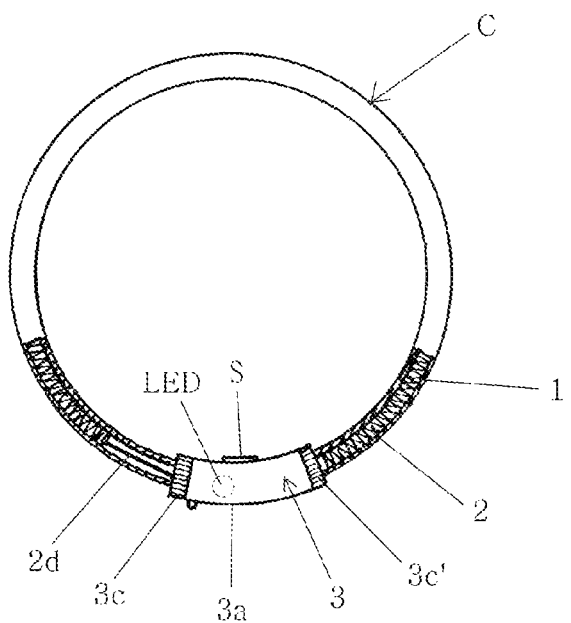
FIG. 1 is a front view illustrating a ring-type cuff according to an embodiment of the present invention.

The present invention is directed to a ring-type cuff for blood pressure manometer comprising a circular rubber ring (1) wearable on a wrist or an ankle, a resilient coil spring (2) built-in inside the circular rubber ring (1) in the range of length of the circular rubber ring (1) to obtain a predetermined flexibility, to suppress excessive stretching, to strengthen durability, and to maintain resilience, and a measurement portion (3) comprising a pressure sensor (S) for measuring blood pressure, a transmission circuit (IC) for transmitting measurement data, a power source (v), and a power switch (sw), wherein the blood pressure is measured by the pressure sensor (S) fixed on the measurement portion (3) of the ring-type cuff and the measurement data is transmitted by the transmission circuit (IC) to an outside unit (4).

The measurement portion (3) of the aforesaid ring-type cuff further comprises a tubular unit (3a) that has a first cap (3c) and a second cap (3c') positioned on both sides of the tubular unit (3a) and combined with the both sides of the tubular unit (3a) via screws, the first cap (3c) is connected to the resilient coil spring (2) through a tension rod (2d) that enables the power switch (sw) to be on by a tension force of the resilient coil spring (2), and the second cap (3c') is connected to the resilient coil spring (2) via a fixed connector (2a).

The pressure sensor (S) provided in the measurement portion (3) of the aforesaid ring-type cuff is positioned toward a radial direction of the circular rubber ring (1) so that the pressure sensor (S) is able to contact skin to measure the blood pressure.

The measurement portion (3) of the aforesaid ring-type cuff further comprises a pilot ramp (LED) to display a mode of the power switch (sw) and a jackhole (jh) that is wired to a transmission circuit (IC) to transfer the measurement data.

The present invention relates to a ring-type cuff for blood pressure manometer, wherein the cuff (C) comprises: a circular rubber ring (1) wearable on a wrist or an ankle; a resilient coil spring (2) built-in inside the tubular rubber ring (1) in the range of length of the rubber ring to obtain a predetermined flexibility, to suppress excessive stretching, to strengthen durability, and to maintain resilience; and a measurement portion (3) comprising a pressure sensor (S) for measuring blood pressure, a transmission circuit (IC) for transmitting measurement data to the outside, a power source (v), a power switch (sw), and a pilot lamp (LED).

EMBODIMENTS

The preferred embodiments of the present invention will be explained in detail with reference to the accompanying drawings.

FIG. 1 is a front view illustrating a ring-type cuff according to an embodiment of the present invention. As shown in FIG. 1, the cuff is a circular rubber ring (1) wearable on a wrist or an ankle. The circular rubber ring is 60 mm to 80 mm in diameter and 5 cm to 8 cm in the thickness. Inside the circular rubber ring (1), there is a resilient coil spring (2) built-in in the range of length of the circular rubber ring (1) to obtain a certain flexibility (1.5~2 times flexibility), to suppress excessive stretching, to strengthen durability, and to maintain resilience.

Figure 2:
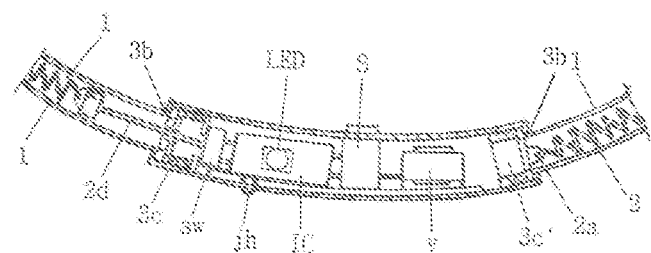
FIG. 2 is an illustrative view describing a measurement portion of the ring-type cuff according to an embodiment of the present invention.

FIG. 2 is an illustrative view describing a measurement portion of the ring-type cuff according to an embodiment of the present invention. As shown in FIG. 2, a measurement portion (3) is located at a predetermined portion of the ring-type cuff (C) and has a first cap (3c) and a second cap (3c') positioned on both openings (3b). The first (3c) and second caps (3c') are combined with the measurement portion (3) with screws. The first cap (3c) is connected to the resilient coil spring (2) through a tension rod (2d) that enables the power switch (sw) to be on when a tension force of the resilient coil spring (2) is working, and the second cap (3c') is connected to the resilient coil spring (2) via a fixed connector (2a).

A circuit board is installed with a pressure sensor (S) for measuring blood pressure, a transmission circuit (IC) for sending measured data to the outside, a pilot ramp to display a status of operation, a power source (v) and a power switch (sw). The circuit board is inserted into the measurement portion (3) through one side of the openings (3b) while the second cap (3c') is open.

The ring-type cuff (C) of the present invention can be used in wired or wireless blood pressure manometers. Especially, the present invention can be used with the 'auto-diagnostic blood manometer' (4) of the aforesaid Korean Patent Gazette No. 10-1081659.

Figure 3:
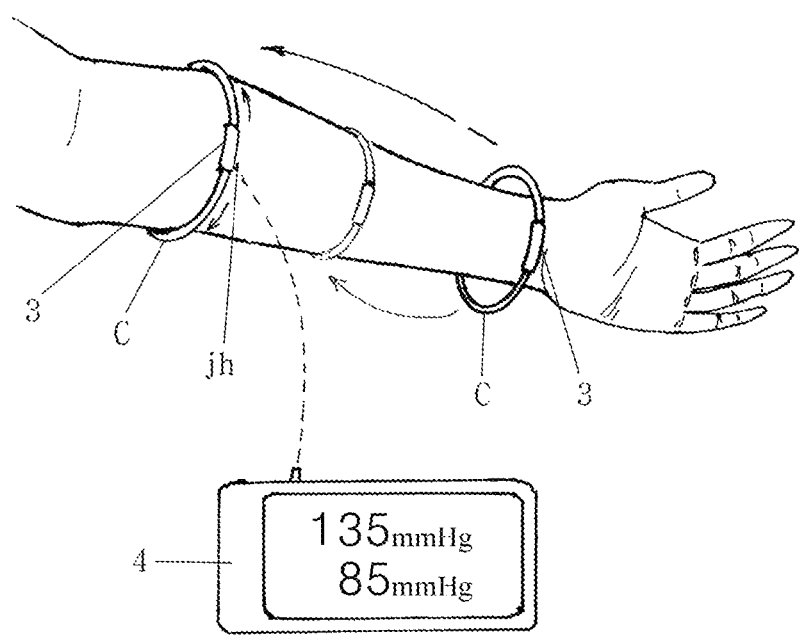
FIG. 3 is an illustrative view describing use of the ring-type cuff to measure blood pressure according to an embodiment of the present invention.
Figure 4:
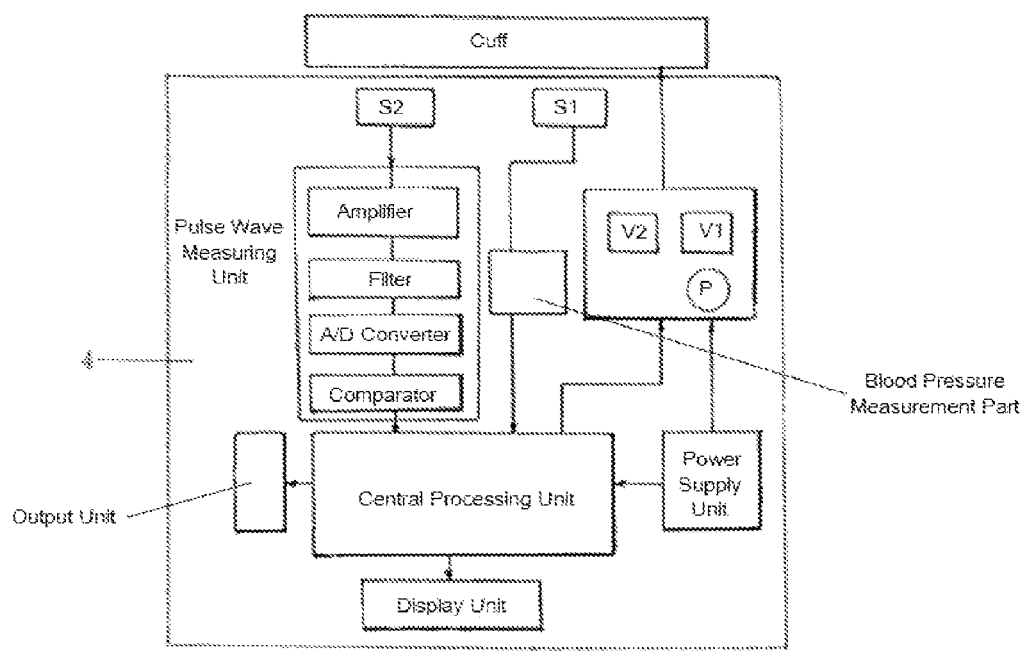
FIG. 4 is a block diagram illustrating a blood pressure measurement system of aforesaid Korean Patent Gazette No. 10-1081659 that applies the present invention.

FIG. 3 is an illustrative view describing use of the ring-type cuff (C) to measure blood pressure according to an embodiment of the present invention. As shown in FIG. 3, the ring-type cuff (C) of the present invention takes the form of bracelet. Thus, one ordinarily wears the ring-type cuff around his or her wrist or ankle. Because the ring-type cuff (C) is light, it is not an obstacle to human activities. Furthermore, because the diameter of ring-type cuff is larger than that of the wrist or ankle, the tension force does not act on the ring-type cuff (C) while it is worn on the wrist or ankle. Thus, there are no procedures such as measuring blood pressure. The power consumption of the ring-type cuff is also minimal.

As shown in FIG. 3, when measuring blood pressure, one can move the ring-type cuff toward his or her forearm or calf. At this time, the ring-type cuff (C) increases its size to the outer side of radius in response to the change of the size of measuring site on the human organism. And then, the ring-type cuff (C) is fixed with a self-elastic supporting force at the measuring site. At this moment, the pressure acting on the measuring site of the human organism by the ring-type cuff (C) is light, only 30 g to 100 g to the whole length of the ring-type cuff. As the size of the ring-type cuff increases, the power switch (sw) of the measurement portion is electrically connected on through a tension rod (2d) by the tension force and the pressure sensor (S) is activated so that the blood pressure can be measured at the location where the ring-type cuff (C) is fixed.

The transmission circuit (IC) sends the measured blood pressure data measured by the pressure sensor (S) to the outside. And then, the central control unit of the 'auto-diagnostic blood manometer' (4) of the aforesaid patent inputs and analyzes the measured data. According to the result of analysis, the display unit presents the name of disease on a display portion.

When the ring-type cuff of the present invention is applied to a wired manometer, the jack hole of the measurement portion (3) connects, through a plug, the ring-type cuff and the wired manometer over a conducting wire.

Regardless of whether it is a wired or wireless manometer, the blood pressure or name of disease measured by the measurement portion (3) of the ring-type cuff in the present invention can be displayed through a letter or a figure on a display portion.

After the blood pressure is measured, if the ring-type cuff (C) is moved back to the wrist or ankle where the ring-type cuff (C) was originally positioned, the ring-type cuff returns to the original state as it contracts its tension force. And then the power switch is disconnected, thereby suppressing the power consumption. Thus, using the present invention, one who wears the ring-type cuff is able to measure his or her blood pressure repeatedly or frequently with a simple operation.

INDUSTRIAL APPLICABILITY

The present invention is directed to a ring-type cuff for blood pressure manometer in a medical field improving heath of human body. The ring-type cuff is worn around the wrist or ankle so that one who wears the ring-type cuff is able to measure his or her blood pressure repeatedly or frequently with a simple operation. The name of disease measured by the present invention can be displayed through a letter or a figure on a display portion.

The invention claimed is:

1. A ring-type cuff for blood pressure manometer comprising:
    a circular rubber ring (1) wearable on a wrist or an ankle;
    a resilient coil spring (2) having a first circumference and a second circumference built-in inside the circular rubber ring (1) in the range of length of the circular rubber ring (1) to obtain a predetermined flexibility, to suppress excessive stretching, to strengthen durability, and to maintain resilience;
    a measurement portion (3) is located at a predetermined portion of the ring-type cuff comprising:
        a pressure sensor (S) for measuring blood pressure;
        a transmission circuit (IC) for transmitting measured data; a power source (v); and
        a power switch (sw) having an "on" position, in which power consumption is activated and an "off" position, in which power consumption is deactivated;
    wherein the measurement portion (3) further comprises a tubular unit (3a) in which a first cap (3c) and a second cap (3c') are positioned on both ends in combination with screws, the first cap (3c) is connected to the power switch (sw) through a tension rod (2d)
    wherein the other end of the tension rod is connected to the resilient coil spring
    wherein the blood pressure is measured by the pressure sensor (S) fixed on the measurement portion (3) of the ring-type cuff and the measured data is transmitted by the transmission circuit (IC) to an external sphygmomanometer (4); and
    wherein the power switch (sw) is configured to be in the "off" position when the resilient coil spring has the first circumference and in the "on" position when the resilient coil spring is stretched by tension force to the stretched second circumference, and again in the "off" position when the resilient coil relaxes back to the first circumference; and
    wherein the pressure sensor can measure blood pressure when the power switch (sw) is in the "on" position and cannot measure blood pressure when the power switch (sw) is in the "off" position.

2. The ring-type cuff of claim 1, wherein the second cap (3c') is connected to the resilient coil spring (2) via a fixed connector (2a).

3. The ring-type cuff of claim 1 wherein the pressure sensor (S) provided in the measurement portion (3) is positioned toward a radial direction of the circular rubber ring (1) so that the pressure sensor (S) can contact skin of a measurement site to measure blood pressure.

4. The ring-type cuff of claim 1 wherein the measurement portion (3) further comprises a pilot ramp (LED) to display a mode of the power switch (sw) and a jackhole (jh) to transmit the measured data over wires to a sphygmomanometer.

5. The ring-type cuff of claim 1, further configured to connect to the external sphygmomanometer wirelessly.

6. The ring-type cuff of claim 1, further configured to connect to a display portion and to display a medical diagnosis on the display portion.

7. A cuff for a blood pressure manometer comprising:
    a support member configured and dimensioned to be wearable on a human limb;
    a resilient coil member having a circumference and being connected to the support member, the resilient coil member having an inactive state and an active state, where the resilient coil member can be moved from the inactive state to the active state by increasing the circumference;
    a measurement portion is located at a predetermined portion of the support member having:
        a pressure sensor configured to measure blood pressure data;
        a transmission circuit configured to transmit the measured data to an external sphygmomanometer;
        a power source;
        wherein the measurement portion further comprises a tubular unit in which a first cap is positioned at a first end and a second cap is positioned on a second end, the first cap is connected to the power switch (sw) through a tension rod;
        wherein the other end of the tension rod is connected to the resilient coil spring; and
    a power switch having an "on" position and an "off" position, wherein when the resilient coil member is in the active state, the power switch is in the "on" position, and when the resilient coil member is in the inactive state, the power switch is in the "off" position
    wherein the power switch is configured to be in the "off" position when the resilient coil spring has the first circumference and in the "on" position when the resilient coil spring is stretched by tension force to the stretched second circumference, and again in the "off" position when the resilient coil relaxes back to the first circumference; and
    wherein the pressure sensor can measure blood pressure when the power switch is in the "on" position and cannot measure blood pressure when the power switch is in the "off" position.

8. The cuff of claim 7, wherein the support member is configured to be wearable on an arm.

9. The cuff of claim 7, wherein the support member is configured to be wearable on a leg.

10. The cuff of claim 7, wherein the support member is a unitary support member having no open end.

11. The cuff of claim 10, wherein the support member has a circumference.

12. The cuff of claim 11, wherein the support member is substantially circular.

13. A method of measuring blood pressure, comprising:
positioning a cuff for a blood pressure manometer on a body, the cuff having:
a resilient coil member having a circumference;
a measurement portion having a pressure sensor;
and a power switch having an "on" position and an "off" position, wherein when the resilient coil member stretches to a first circumference, the power switch is in the "on" position, and when the resilient coil member shrinks to less than the first circumference, the power switch is in the "off" position;
wherein the pressure sensor can measure blood pressure when the power switch is in the "on" position and cannot measure blood pressure when the power switch is in the "off" position;
moving the cuff to a location on the body having a surface to measure blood pressure, such that the pressure sensor contacts the surface, and stretching the resilient coil member to the first circumference so as to activate the power switch to the "on" position; and
collecting blood pressure data at the surface of the body using the pressure sensor.

14. The method of claim 13, further comprising the step of transmitting the blood pressure data to an external sphygmomanometer.

15. The method of claim 13, including, after the step of collecting blood pressure data, the step of moving the cuff away from the location on the body such that the resilient coil member shrinks from the length so as to put the power switch in the "off" position.

16. The method of claim 13, wherein the cuff is positioned on an arm of a human.

17. The method of claim 13, wherein the cuff is positioned on a leg of a human.

* * * * *